United States Patent [19]
Schafer et al.

[11] Patent Number: 6,029,522
[45] Date of Patent: Feb. 29, 2000

[54] ULTRASONIC APPARATUS FOR CHARACTERIZING WOODEN MEMBERS

[75] Inventors: Mark E. Schafer, Norristown, Pa.; Robert J. Ross, Madison, Wis.

[73] Assignees: Perceptron, Inc., Plymouth, Mich.; The United States of America as represented by the Department of Agriculture, Washington, D.C.

[21] Appl. No.: 09/151,432

[22] Filed: Sep. 11, 1998

Related U.S. Application Data

[60] Provisional application No. 60/076,090, Feb. 26, 1998.

[51] Int. Cl.⁷ ................................................. G01N 29/04
[52] U.S. Cl. ........................... 73/598; 73/587; 73/645
[58] Field of Search ............................. 73/579, 584, 587, 73/596, 597, 598, 599, 600, 645, 646, 632, 635

[56] References Cited

U.S. PATENT DOCUMENTS

| | | | |
|---|---|---|---|
| 4,838,085 | 6/1989 | Pellerin et al. | 73/597 |
| 4,858,469 | 8/1989 | Hosgood et al. | 73/579 |
| 5,024,091 | 6/1991 | Pellerin et al. | 73/597 |
| 5,237,870 | 8/1993 | Fry et al. | 73/588 |
| 5,307,679 | 5/1994 | Ross | 73/597 |
| 5,396,799 | 3/1995 | Ross et al. | 73/579 |
| 5,760,308 | 6/1998 | Beall et al. | 73/644 |
| 5,804,728 | 9/1998 | Beall et al. | 73/598 |

*Primary Examiner*—Hezron Williams
*Assistant Examiner*—Thuy Vinh Tran
*Attorney, Agent, or Firm*—Woodcock Washburn Kurtz Mackiewicz & Norris LLP

[57] ABSTRACT

Ultrasonic techniques are applied to the measurement of wooden members to identify localized anomalies internal to the wooden members substantially smaller than the full width of the ultrasonic beam. Multiple spatially displaced measurements allow generation of comprehensive maps of the wooden members to aid in computer cutting and grading of the wooden members.

14 Claims, 6 Drawing Sheets

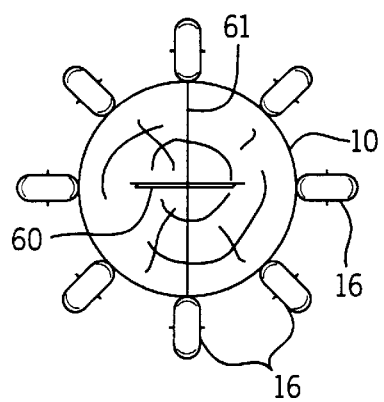
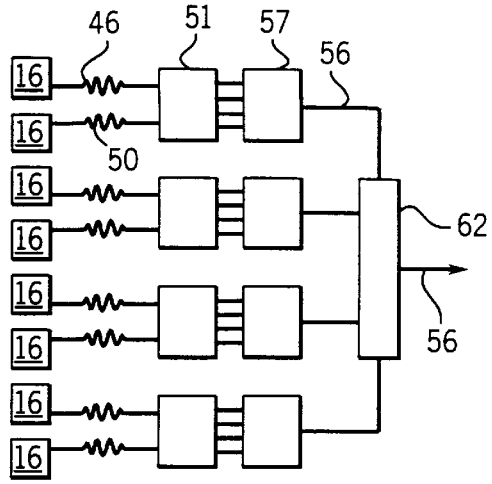
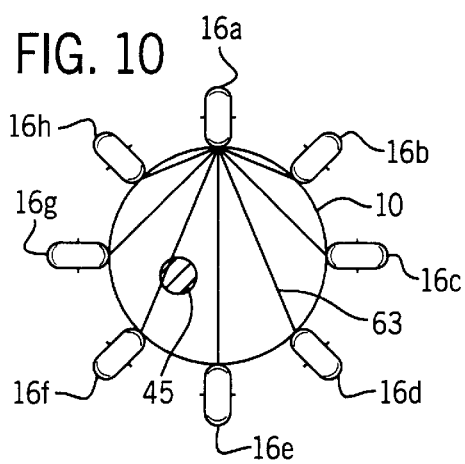
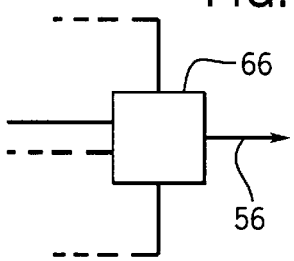
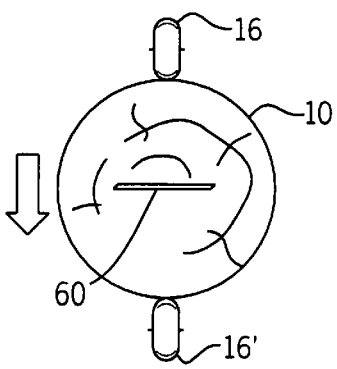
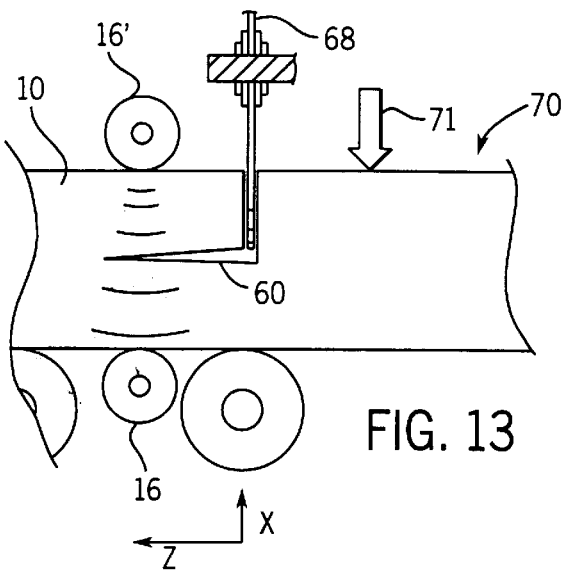

ULTRASONIC APPARATUS FOR CHARACTERIZING WOODEN MEMBERS

CROSS-REFERENCE TO RELATED APPLICATIONS

This application claims benefit of Provisional Application 60/076090 filed Feb. 26, 1998.

STATEMENT REGARDING FEDERALLY SPONSORED RESEARCH OR DEVELOPMENT

BACKGROUND OF THE INVENTION

The present invention relates to an apparatus for the detection of localized anomalies or other localized features in wood, such as knots, splits, voids, checks, and localized decay for the purpose of grading or cutting wood products such as lumber, and specifically to an apparatus employing ultrasonic energy to characterize both dried and undried wooden members. The wooden members may be trees, logs, beams, planks, lumber, boards or wood composites and the like.

Ultrasound has been used to characterize the gross properties of wooden members through measurement of time of flight, attenuation, and attenuation as a function of frequency (broadband ultrasonic attenuation) of ultrasound passing through a wooden member. For example, U.S. Pat. No. 5,307,679 to Ross and assigned to the United States of America, describes the use of ultrasonic measurements to detect a proclivity of a wooden members to degrade during the drying process. Another example includes identifying naturally occurring defects to aid in lumber grading for both structural and non-structural applications.

It is also desirable to detect, identify and locate smaller anomalies in wooden members such as knots, checks and splits. Such defects, when identified, can be input to commercially available optimization systems to allow for the sorting or cutting of the wooden members in a way so as to maximize their value, for example, by cutting a log to produce the maximum number of board feet of clear or higher grade lumber.

Traditionally identification of defects and other features affecting lumber grade has been performed visually, for example, by a saw operator visually inspecting the log or board prior to determining the necessary cross or rip cuts that will yield the best product output or yield. Recently a number of electronic scanning systems have been produced using cameras and lasers to automate this visual process. Such optical techniques are limited to the detection of superficial defects in the wooden members and even these techniques may be defeated by dirt, bark, stain or other markings on the outside of the log. More importantly, internal defects are generally not visible externally, yet may affect product performance or value.

What is needed is an apparatus for detecting and identifying localized anomalies even internal to a wooden member, that is also robust against the harsh environment of a typical sawmill or the like and that is safer, less costly and more compact than instruments based on x-rays or other electromagnetic radiation, or which provide information which those systems have difficulty in detecting such as splits and checks.

BRIEF SUMMARY OF THE INVENTION

The present inventors have discovered that localized defects such as knots, checks and splits or other features such as slope of grain may be detected by a distortion of an ultrasonic beam when a part of the beam passing through the localized defect interferes with a part of the beam passing through clear or sound wood in either the dried and undried states. This distortion may be detected by measurement of waveform spreading, decorrelation techniques or other similar techniques. If the defect or condition is of broader extent than the ultrasound beam, then the defect or condition may be detected by comparison of the signals made in clear portions of the wooden member, in regions where the ultrasound beam is completely intercepted by the defect or condition, and in regions at the edge of the defect or condition wherein the ultrasound beam passes through both the condition or defect and clear or sound wood. Multiple transducers and receivers providing additional beams coupled to the wooden member and moving relative to it allow both detection and more accurate localization of localized anomalies or other features.

Specifically, the present invention provides an apparatus for detecting localized defects in wooden members and includes at least one pair of opposed ultrasonic transducers positionable about the wooden member so that an axis between the transducers is oriented substantially perpendicular to the grain of the wooden member. Electronic driving circuitry drives one of the ultrasonic transducers so as to produce an ultrasonic wave of known characteristics having a beam width through the wooden member. A detection circuit connected to the output of another of the ultrasonic transducers receives the ultrasonic wave after passage through the wooden member along either singular or multiple paths in the beam width. An electronic computer communicating with the driving and detecting circuits executes a stored program to compare the received ultrasonic wave against a standard to detect a distortion in the waveform caused by variation in the wooden member within the region defined by the ultrasound beam width. Based on a detection of this distortion, the computer provides an output indicating the presence of localized defects or other conditions. The waveform pattern can also be used to identify the condition which caused the waveform distortion, and to localize that condition as the transducers are moved relative to the wooden member.

Thus, it is one object of the invention to provide an ultrasonic apparatus for detecting localized conditions within a wooden member useful for characterizing the member for sawing or grading.

The comparison performed by the apparatus may address the attenuation of total energy in the received ultrasonic wave, the change in spectral energy distribution in the received ultrasonic wave, the spreading of the temporal distribution of energy in the received ultrasonic wave, phase distortion in the received ultrasonic wave or a combination of the above.

Thus it is another object of the invention to provide for a multiparameter measurement so as to improve the accuracy and robustness of the ultrasonic measurements.

The apparatus may use multiple ultrasonic transducers whose outputs may be collected or the measurements may be repeated with a single pair of ultrasonic transducers.

Thus it is another object of the invention to employ multiple transducer measurements so as to improve the accuracy and robustness of the detection process.

The apparatus may include a means for measuring the thickness of the wooden members along the axis and may calculate a time of flight of the ultrasonic wave between transducers to determine a sound velocity, or may determine a change in energy or phase as a function of thickness.

Thus it is another object of the invention to account for other factors affecting the received ultrasonic waveform so as to improve the apparatuses ability to detect localized defects or other features within wooden members of varying thickness and type.

The apparatus may include a means for moving the wooden members with respect to the ultrasonic transducers perpendicular to the axis of the transducers and the output of the electronic computer may be a measure of wooden members' quality as a function of position.

Thus it is another object of the invention to locate anomalies along the length of a wooden member for the purpose of guiding a cutting of the wooden member to optimize its usage.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention.

BRIEF DESCRIPTION OF THE SEVERAL VIEWS OF THE DRAWINGS

FIG. 8 is a figure similar to FIG. 5 showing transducers arrayed radially around the circumference of the wooden member such as may be useful for the detection of internal splits or checks;

FIG. 9 is a block diagram similar to that of FIG. 3 showing the repetition of the element of FIG. 3 for each of the transducers of FIG. 8 and collected by a parameter extraction block identifying an orientation of a split;

FIG. 10 is a figure similar to that of FIG. 8 showing the use of the transducer assembly of FIG. 8 for tomographic analysis of the internal structure of the wooden member;

FIG. 11 is a fragmentary view of FIG. 9 showing a tomographic back projection block used to replace the parameter extraction block of FIG. 9 when the assembly of FIG. 8 is used for tomographic analysis;

FIG. 12 is a figure similar to that of FIGS. 8 and 10 showing the wooden member in cross section along the x-y plane with a single pair of transducers positioned for the detection of dynamic splits caused by a sawing operation;

FIG. 13 is a view of the wooden member of FIG. 12 along the x-z plane showing a development of a dynamic split with respect to the transducers of FIG. 12 during the cutting operation caused by the cantilevered weight of the end of the wooden member;

DETAILED DESCRIPTION OF THE INVENTION

Figure 1:
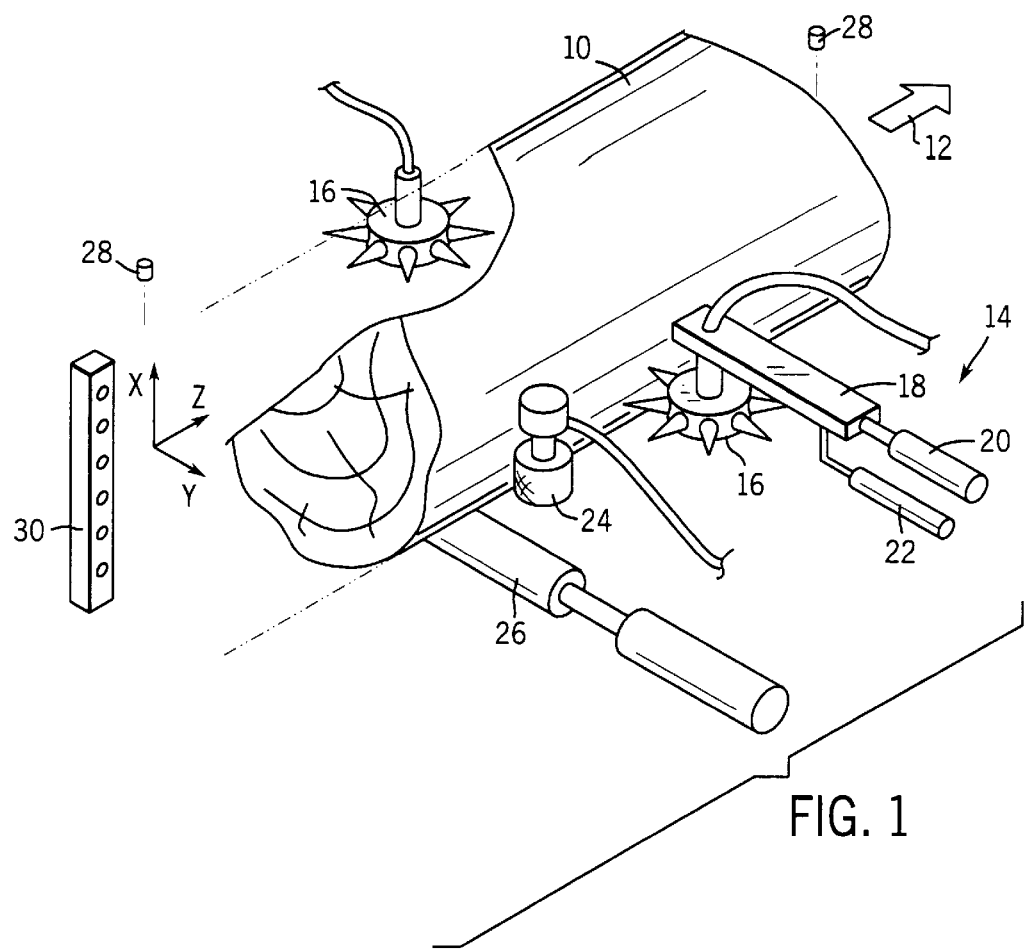
FIG. 1 is a perspective view in partial cutaway of a wooden member as may be moved in a translation direction with respect to opposed ultrasonic transducers incorporated into wheels and pressed against the opposed sides of the wooden member, FIG. 1 further showing other sensing devices for characterizing the wooden members' shape and position.

Referring now to FIG. 1, a wooden member 10 such as a log is shown positioned horizontally so that its grain direction and axis define a z-axis of a Cartesian coordinate system with the x-axis directed generally upward and the y-axis horizontal. As will be understood from the following description, the term wooden member should be held to embrace trees, logs, lumber, boards and wood composites in various stages of processing.

The wooden member 10 may be moved in a translation direction 12 with respect to a measurement assembly 14 by one or more driven rollers 26 that support the wooden member 10 from underneath. In some instances (not shown here), the wooden member may be rotated.

The measurement assembly 14 includes a first (transmitting) and second (receiving) ultrasonic transducer 16 encased in rollers such as may roll against the surface of the wooden member 10 as it moves in the translation direction 12. The ultrasonic transducers 16 are opposed along the y-axis to transmit and receive an ultrasonic signal through the wooden member 10 radially and perpendicular to the grain, and are attached to slide assemblies 18 (only one shown) which are biased toward the wooden member 10 by an air cylinder 20 or the like. The wheels of the transducers 16 thereby maintain contact with the outer surface of the wooden member 10 while being free to rotate about their axes.

A linear position sensor 22 may be attached to the slide assembly 18 so as to provide a measurement of the separation of the transducers 16 and hence a measurement of the width of the wooden member 10 along the axis between the transducers 16. An encoder/roller assembly 24 positioned against the outer surface of the wooden member 10 provide a measurement of the z-axis position of the wooden member 10 as it moves in the translation direction 12. Auxiliary sensors, such as photoelectric proximity sensors 28, may be positioned separated along the z-axis and directed downward along the x-axis to detect the beginning and end of the wooden member 10 as it moves, and thus to provide a measurement of its length. A sensor array 30 having multiple photoelectric sensors arrayed along the x-axis may provide a height measurement of the wooden member 10 along the x-axis to further characterize the wooden member 10.

Ultrasonic transducers encased in a wheel and suitable for use in this application with regular wooden members such a boards and logs stripped of bark, are commercially available from James Instruments of Chicago, Ill. (Model C-7219) and Dapco Industries of Ridgefield, Conn. The transducers may be oriented to produce either longitudinal or shear waves through the wooden member 10.

Figure 15:
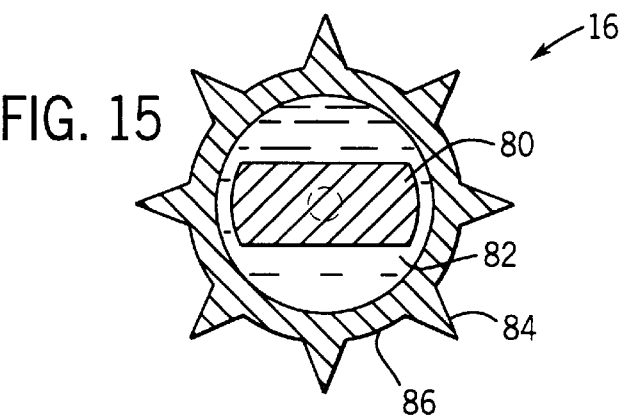
FIG. 15 is a cross sectional view of a transducer of FIG. 1 having a spiked outer collar for penetration of bark and or for better coupling with the wooden member.

Referring momentarily to FIG. 15, in a preferred embodiment, the ultrasonic transducers 16 includes a transducer element 80 held in a coupling fluid such as oil 82 as contained by the inner surface of a rotating wheel 86 as is done in the commercially available transducers 16 described above. In distinction, however, the outer surface of the wheel provides a series of radially extending spikes 84 whose sharpened tips may embed themselves in the wooden member to better couple ultrasonic energy into and out of the wooden member and to penetrate bark and the like which generally inhibit the transmission of ultrasonic energy. The sharpened tips of the spikes concentrate pressure to provide improved penetration.

Figure 2:
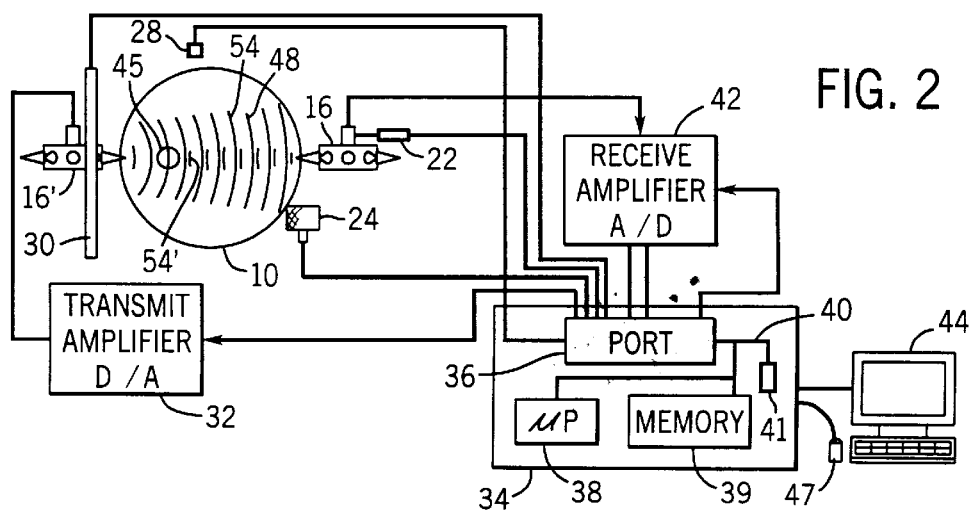
FIG. 2 is a block diagram showing the transducers and wooden member of FIG. 1 together with associated processing circuitry for generating and receiving ultrasonic signals and processing the same including an electronic computer having a standard computer monitor and keyboard.

Referring now to FIG. 2, the invention operates under the control of a standard desk top computer 34 such as a so called "Wintel" computer using the Windows operating system and an Intel 133 MHz Pentium processor chip set. Computer 34 includes a port 36, a processor 38, and electronic memory 39 of a type familiar to those of ordinary skill in the art, all interconnected by an internal bus 40. The port 36 accepts input digital signals from devices outside the computer 34 and provides output digital signals to devices outside the computer as generated by execution of a stored program as will be described. The principal output signal generated is a digitized ultrasonic pulse waveform, which is communicated through the port 36 to an amplifier/D to A converter 32. The amplifier/D to A converter 32 converts the digitized ultrasonic pulse waveform to a high power analog electrical signal that is output to one 'transmitting' ultrasonic transducer 16 to drive the transmitting ultrasonic transducer 16' to produce a predetermined broadband ultrasonic pulse of predetermined phase and frequency content, in the preferred embodiment having a center frequency of substantially 80 kHz. It will be understood to those of ordinary skill in the art that other frequencies may also be used.

The port 36 also receives inputs from receiving transducer 16 detecting the ultrasonic waveform after it has passed through the wooden member 10 as pre-processed by a gain-controllable amplifier/A to D converter 42. Gain-controllable amplifier/A to D converter 42 preferably provides at least eight-bits of resolution and a sampling speed of at least 2.5 times the center frequency of the ultrasonic waveform being transmitted. The gain-controllable amplifier/A to D converter 42 provides for amplification over a fifty dB range as controlled by the computer 34.

Port 36 also receives inputs from the proximity sensors 28 and 30, the linear position sensor 22, the encoder/roller assembly 24, and the sensor array 30 so as to make their measurements available to the computer 34. A separate port 41 connects the computer 34 to the standard computer monitor 44 and keyboard/mouse 47.

During operation of the apparatus of the present invention, the computer 34 executes a stored program held in memory 39 to cause the transmission of the broadband ultrasonic pulse from transducer 16' to transducer 16. The computer 34 then collects and processes the data from transducer 16 receiving the ultrasound pulse after transmission through and modification by the wooden member 10, as well as inputs from the other sensors to evaluate the wooden member 10. The rate at which the computer controls the amplifier/D to A converter 32 to transmit the broadband pulse is determined by the desired spatial sampling rate, and the speed of the wooden member 10 as it is moved into the translation direction 12. In one embodiment, the computer controls the amplifier/D to A converter 32 so as to transmit the broadband pulse thirty-two times per second providing a sampling of the wooden member 10 as it is moved in the translation direction 12, every 0.12 inches, assuming a twenty foot per minute speed of the wooden member 10.

The effective aperture of the transmitting and receiving ultrasonic transducers 16' and 16, and the sound transmission properties of the wooden member 10 define an effective beam 48 through the wooden member 10 along which measurements will be made. The wooden member 10 may include a localized anomaly 45, such as a knot or check, which may or may not significantly affect the overall strength of the wooden member 10. In the case shown, the localized anomaly 45 has a size substantially less than the width of the beam 48. Accordingly, it will be expected that a portion 54 of the beam 48 will miss the localized anomaly entirely, significantly reducing the contribution of the localized anomaly 45 on any modification of the beam 48 by the wooden member. Thus an interference occurs between the sound 54' traveling though the anomaly 45 and the sound 54 traveling through unaffected wood. Alternatively, a narrow beam may be used such as will be substantially completely intercepted by the anomaly. Further, for the case in which the wooden member is a board, and the ultrasound transducers are disposed on either edge, the anomaly may encompass the entire lateral dimension of the wooden member, completely intercepting the ultrasound beam regardless of the beam width. In either case, signals may be compared against a standard signal taken at an earlier or later time of unaffected wood or derived from a model of unaffected wood.

Figure 3:
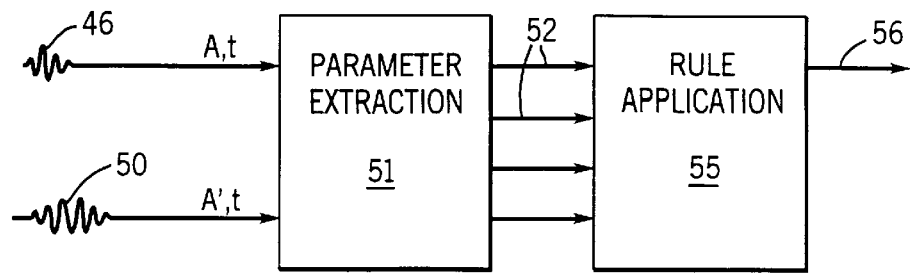
FIG. 3 is a schematic representation of a processing program executed by the computer of FIG. 2 receiving an ultrasonic waveform through the wooden member and comparing it to a transmitted ultrasonic waveform passing through a standard material to produce multiple measurement parameters which may be combined to detect localized anomalies.
Figure 17:
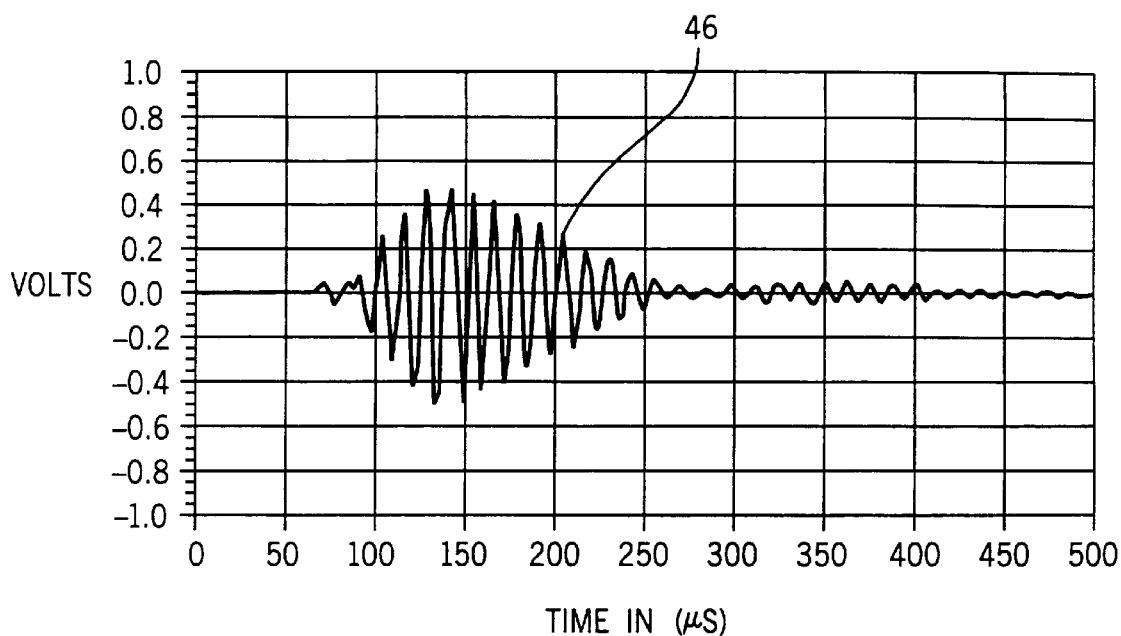
FIG. 17 is a graph of signal voltage vs. time for a representative waveform of FIG. 3 passing through the standard material.
Figure 18:
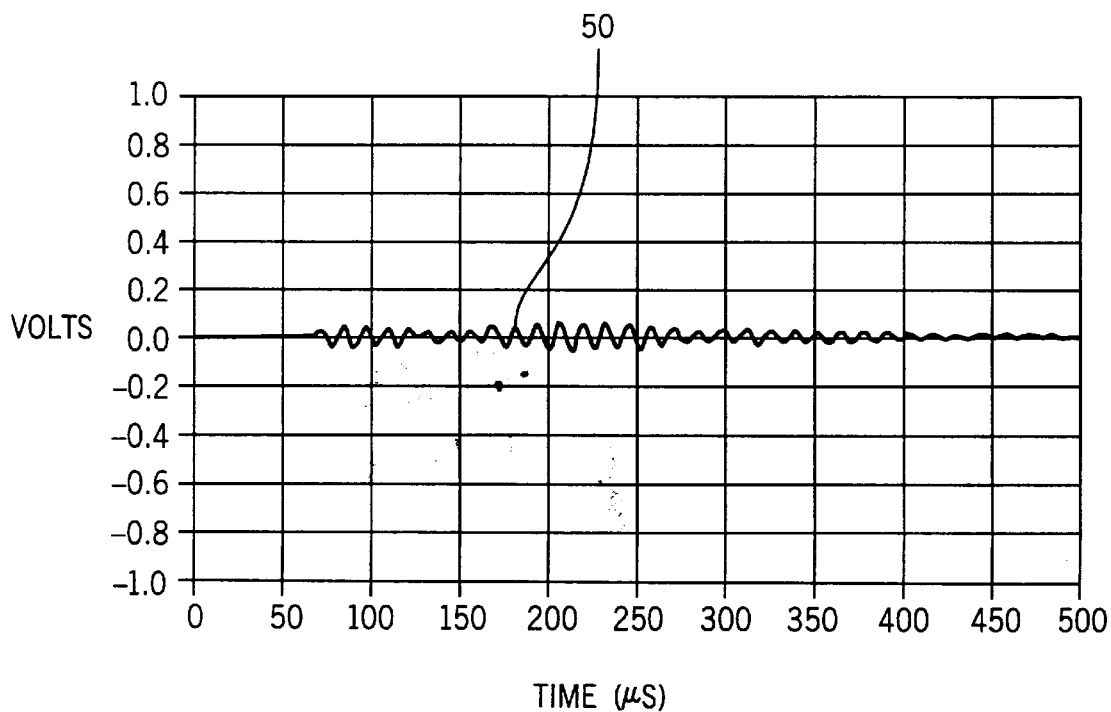
FIG. 18 is a graph of signal voltage vs. time for a representative waveform of FIG. 3 passing through the wooden member being evaluated.

Referring now to FIG. 3 and 17, the standard waveform 46 derives from a digitized version stored within the memory 39 as ordered pairs of amplitude values (A) having distinct times values (t). The standard waveform 46 represents a waveform received through a standard material without localized anomalies, such as clear wood or plastic. The received waveform 50, (shown also in FIG. 18) being an actual measurement of the wooden member 10, may be similarly stored in memory 39 as a set of received amplitude values (A') at later time values (t) the delay resulting generally from the transit time in the passage of the waveform through the wooden member 10.

Figure 6:
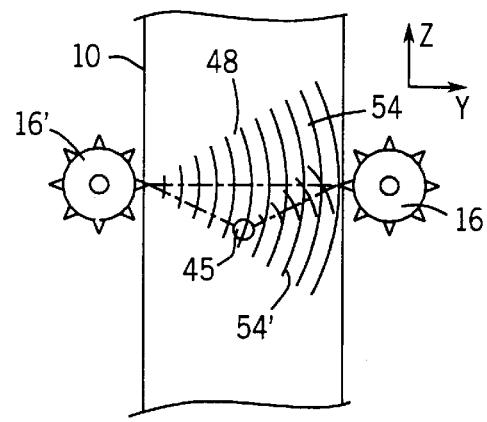
FIG. 6 shows a plan view in cross section of the wooden member and transducers of FIG. 1.

Referring to FIG. 3 and 6, the two waveforms of the standard waveform 46 and received waveform 50 are then analyzed according to a number of different techniques to produce parameters 52. Specifically, and referring again to FIG. 2, the present inventors have recognized that even though the localized anomaly 45 may be relatively small in comparison to the total width of the ultrasound beam 48, a portion of the beam 48 passing along a path 54 through the localized anomaly 45 modifies the remaining portion of the beam 48 passing along a path 54' outside the localized anomaly 45, the resulting interference modifying the received waveform 50 in phase and amplitude or other characteristics in a manner that may be detected and analyzed. Similarly, the ultrasound beam 48 may only pass through a portion of the localized anomaly 45, irrespective of the size of the localized anomaly 45, depending upon the orientation of the ultrasound beam 48, which also results in interference modifying the received waveform 50. This analysis involves extracting various parameters 52 from the received waveform 50 each parameter 52 selected to detect a distortion in the received waveform 50 caused by interference between waveforms on different paths 54 and 54'.

A basic parameter is that of the spreading of the received waveform 50 with respect to the standard waveform 46 caused by variation in the effective path lengths 54 and 54' (caused both by differences in path length and differences in sound speed) such as tends to spread the received waveform 50 in time. Pulse length is defined in the preferred embodiment as 1.25 times the time required for the received wave energy integral to rise from ten percent to ninety percent of its final value. Wave energy as understood in the art is determined by the formula $$WE = \int v^2(t)dt. \quad (1)$$

where v is the voltage produced by the transducer 16 and t is time. The pulse length of the received waveform 50 is compared against the pulse length of the standard waveform 46 calculated in a similar manner to produce the relevant parameter.

The effect of the localized anomaly 45 may also change the insertion loss between the two transducers 16' and 16. This forms a second parameter of the measurement and is defined as the ratio of the energy received by the transducer 16' to the energy input into the wooden member 10 by the transducer 16 according to the following formula:

$$IL(db) = 10 \log[E_r/E_t]G \quad (2)$$

where Er is the received energy, $E_t$ is the transmitted energy, and G is the receiver gain as may be programmed as described above. Insertion loss may be further compared to a reference value taken through a standard of known acoustic properties such as a clear wooden members or a standard reference material such as water or homogenous plastic block. Insertion loss may be further compared as a function of the distance that the ultrasound wave travels through the wooden member (using a width measurement from the linear position sensor 22), expressed in Decibels per inch (or decibels per centimeter).

A third parameter may be the time of flight of the pulse determined by a correlation of the transmitted and received waveforms 46 and 50 such as may provide an indication of the overall qualities of the wooden member 10 outside of the localized anomaly 45. This time of flight value may alternatively be divided by a width measurement from the linear position sensor 22 to produce a sound velocity measurement.

A fourth parameter uses a deconvolution of the received waveform 50 by the standard waveform 46 which may be expressed mathematically as either $$FFT^{-1}\left(\frac{\text{Cross Power(Reference, Unknown)}}{\text{Power Spectrum(Unknown)}}\right) \quad (3)$$

or $$FFT^{-1}\left(\frac{FFT(\text{Unknown})}{FFT(\text{Reference})}\right) \quad (4)$$

where FFT and $FFT^{-1}$ are the Fourier transform and the inverse Fourier transform, respectively, and wherein the Unknown is signal through the wooden member 10 and the Reference is a signal through a reference standard of known acoustic properties. This deconvolution allows the detection of multiple signal paths through the wooden member 10 whose variation may indicate the presence of a localized anomaly 45 which creates effectively a new path through the wooden member 10. Other methods such as homomorphic filtering known to those of skill in the art may be used for the same purpose.

Figure 4:
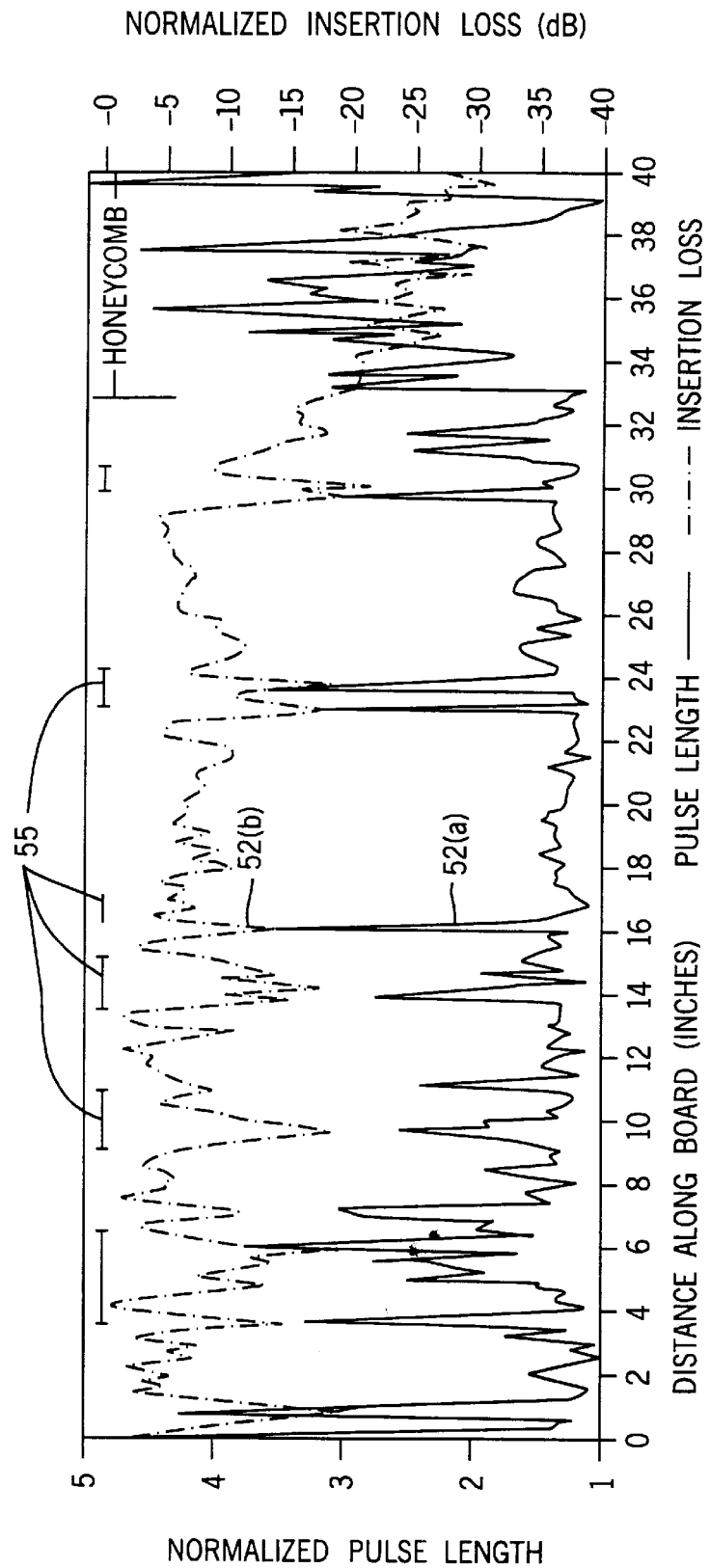
FIG. 4 is a graph of two such parameters, specifically pulse length and insertion loss (defined below), plotted against distance along the translation axis showing the position of local anomalies evident by examination of these two parameters.

Referring now to FIGS. 3 and 4, two or more parameters may be compared over the length of the wooden member 10 along the translation direction 12 to detect localized anomalies 45. In the example of FIG. 4, peaks in pulse length 52(a) and troughs in insertion loss 52(b) correlate to regions 55 in which localized anomalies 45 are found. Accordingly, an empirically derived rule may be developed by testing each of pulse length 52(a) and 52(b) against a threshold and logically ANDing the test outcomes together to produce an output indicating a localized anomaly 45. The rule may be implemented by explicit rules programmed into the computer 34 or may be performed by artificial intelligence techniques such as neural networks or fuzzy logic known in the art. Such rules are shown by rule application block 55 and may combine two or more parameters 52.

The benefits of multiple parameter measurement can be further seen in Table I below for various types of wood conditions.

| Parameter | Normal | Wetwood | Knot | Honeycomb |
|---|---|---|---|---|
| Insertion Loss (dB) | −50 | −70 | −66 | −78 |
| Pulse Length (µs) | 110 | 235 | 244 | 239 |
| Time of Flight | 80 | 90 | 80 | 96 |

Figure 5:
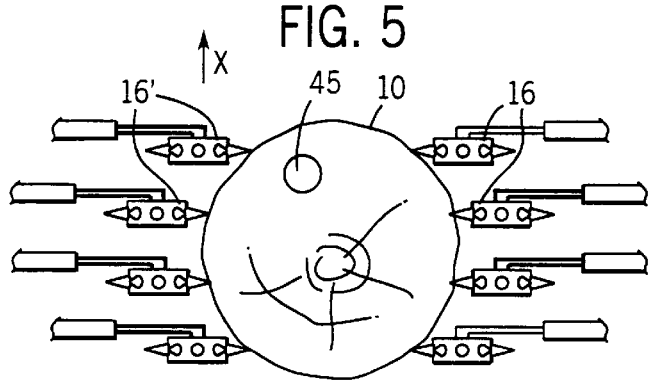
FIG. 5 is an alternative embodiment of the transducer assembly of FIG. 1 showing multiple transducers positioned in an array along an x-axis across the grain of the wooden member to provide improved localization of the internal anomalies of the wooden members.
Figure 16:
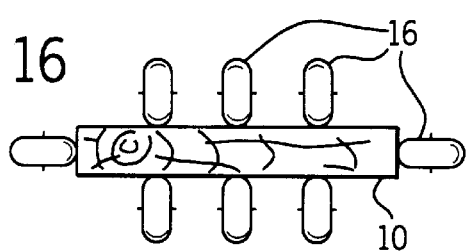
FIG. 16 is a view similar to that of FIG. 5 showing transducers positioned along both the x and y axes about a board.

Referring now to FIG. 5, an array of ultrasonic transducers 16 and 16' may be positioned at varying x-axis locations on the side of the wooden member 10 pairs opposed along different axes both radial and tangential to the wooden member 10 across the grain of the wooden member 10 to provide a different parametric reading for each x-axis location. These transducer arrays provide additional spatial information about the location of a localized anomaly 45 in the x-axis direction. In yet an alternative embodiment shown in FIG. 16, transducers 16 may be placed arrayed along either or both of the x and y-axis to locate the localized anomaly 45 with respect to the x and y-axes. This embodiment is particularly useful for grading lumber as to strength where the location of a knot, as opposed simply to its existence, is important as to its effect on strength. Strength grading can be used to determine the location of pieces of lumber in the final product, for example a pallet, where stronger pieces of lumber are used for the core of the pallet and the weaker pieces of lumber are used for the planking that serves merely to provide the pallet surface. In the embodiment of FIG. 16, individual top transducers 16 may be excited while readings are taken at all bottom transducers 16 so as to obtain measurements along four simultaneous axes for each excitation and reading along sixteen axes for all four top transducers 16. These multiple readings may be used to triangulate the location of the anomaly.

Figure 7:
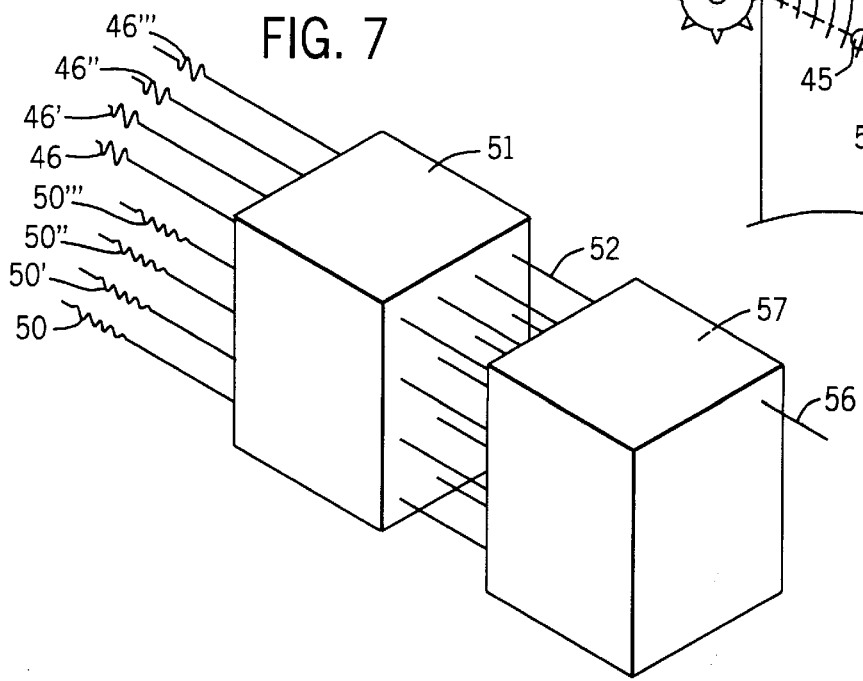
FIG. 7 is a figure similar to that of FIG. 3 showing the multiparametric measurement of FIG. 3 applied to the additional dimension of x or z (the translation axis) in the embodiments of FIGS. 5 and 6 to provide a more robust measurement of localized anomalies.

As shown in FIG. 7, the parameter extraction block 51 for any of these multiple measurement embodiments of FIGS. 6 and 7 will receive a two dimensional array of standard waveforms 46–46" and received waveforms 50–50'". Each corresponding standard and received waveform 46 and 50 may be compared as described with respect to FIG. 3 but in additional cross combinations of the various waveforms may also be used to produce new effective particular parameters such as spatial rates of change of the parameters in the x or z direction.

As before, these parameters 52 may be provided by rule application block 55 to produce an output 56 providing an identification of localized anomalies 45 and further providing additional spatial location of localized anomalies 45 in the x-axis or y-axis.

Specifically, the x- and y-axis positions of localized anomalies 45 may be determined from the parameters derived from the location of individual transducer pair satisfying the rule of rule block 55 in the same way that the z-axis position is determined as described with respect to FIG. 4. In this way, a map of the spatial location of localized anomalies 45 for the entire wooden member 10 may be developed.

Using this map, decisions about length of cuts of the wooden member 10 across the z-axis (to remove localized anomalies 45 from boards) may be augmented with decisions about rip cuts of the wooden member 10 along the z-axis such as to maximize the value of the cut wood by moving localized anomalies 45 among boards.

Referring now to FIG. 8, a set of transducers 16 may be arrayed about the periphery of the wooden member 10 so that the plane of the wheels of each transducer 16 includes the z-axis and extends radially therefrom so as to provide axis 61 between pairs of transducers 16 that extend radially through the wooden member 10. This configuration may be used to identify splits 60 within the wooden member 10 such as have a varying cross section depending on the radial direction along which they are viewed. Thus such splits 60 may be localized to lie narrowly along one radial direction while being relatively broad in another radial direction.

Referring to FIG. 9, each opposed pair of transducers 16 is connected to a parameter extraction block 51 (as described above) so as to provide a plurality of parameters 52 associated with different radial angles. Each parameter extraction block 51 is associated with a rule application block 55 to produce an output 56 for each radial angle. The outputs may be compared by a parameter extraction block 62 to identify the plane of the split as it crosses the x-y axis. In one embodiment, the parameter extraction block 62 may be a simple magnitude comparator. Generally the radial angle associated with the greatest insertion loss will be perpendicular to the plane of the split 60.

Referring now to FIG. 10, in a alternative embodiment to the embodiment of FIG. 7, the consideration of the cross terms of the various standard and received waveforms 46 and 50 and their deduced parameters may be realized with a tomographic reconstruction. In this tomographic reconstruction, each ultrasonic transducer 16, for example, ultrasonic transducer 16(*a*) may sequentially serve as a source of ultrasonic energy to be received by each of the other ultrasonic transducers (*b*) through (*h*). Relatively narrow effective beam widths along projection lines 63 may be obtained in this manner. The standard waveform 46 of the selected ultrasonic transducer 16*a* may be compared pair-wise to the received ultrasonic waveforms 50 of each of the ultrasonic transducers 16*b–h* to produce a separate parameter measurement. The parameters measured may be any of those previously described or other similar measurements.

Referring to FIG. 11, the parameters themselves or rule based combinations of parameters derived from measurements along ones of different projection lines 63 are then provided to a tomographic reconstructor 66 such as is known in the art of x-ray tomography to provide an image of a cross sectional cut through the wooden member 10 in the x-y plane. Such a tomographic reconstructor 66 may use a fan beam, filtered back projection algorithm known in the art. This x-y mapping may augment z-axis information obtained by taking multiple projections at different z-axis locations along the wooden member 10 allowing for multidimensional optimization of the cutting of the wooden members.

Referring now to FIG. 12, in a variation on the embodiment of FIG. 8, a single pair of transducers 16 and 16' may be placed in vertical opposition about the wooden member 10 to detect dynamic splits 60 occurring in a horizontal plane as caused by a cutting of the wooden member 10. Referring also to FIG. 13, such splits may occur when a cut by a saw 68 is made in the x-y plane part way through the wooden member 10 upon which the cantilevered weight of an end 70 of the wooden member 10 exert a downward force 71 causing the split 60. Such dynamic splits caused by force 71 may close after the cut is complete but may still be identified by the technique of FIG. 8. However, by using a concurrent transmission of ultrasonic energy adjacent to the cut line of the saw 68 on the supported side of the wooden member 10 during the cutting process, the split may be detected as it occurs and decisions about the board made in real-time. Again multiple transducers displaced as shown in FIG. 6 may be used to characterize the depth of the split. Appropriate bandpass and time window filtering and choice of measurement parameters may be used to permit the split to be detected without interference from both the electronic an vibrational the noise of the cut of the saw 68. Knowing that the split 60 is occurring may allow saw operator to adjust the sawing procedure to reduce the incidence of splitting. Further knowing the depth of the split with a disposition of the transducers (not shown) along the z axis or the length of the wooden member may allow the operator to adjust the length of the sawn wooden member 70 such that a desired length of un-split wood is produced.

Figure 14:
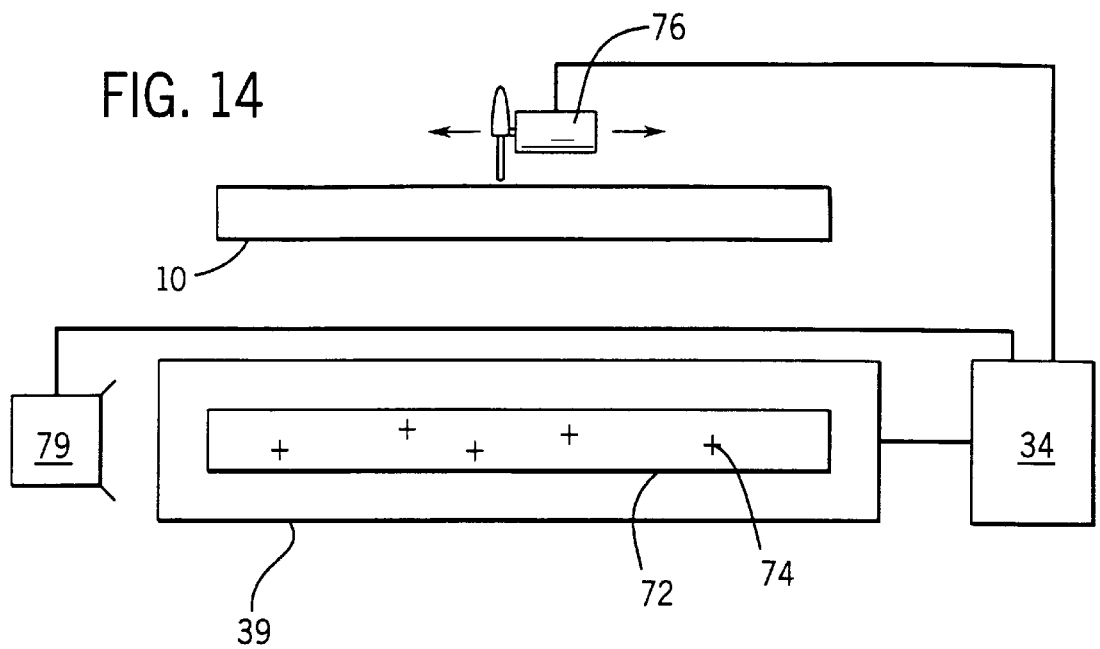
FIG. 14 is a schematic representation of a computer controlled cutoff saw suitable for cutting wooden members as characterized by the present invention so as to optimize usage of wooden members based on the location of identified anomalies.

Referring now to FIG. 14, the present invention provides in the memory 39 of the computer 34 a map 72 of the wooden member 10 indicating sites 74 of local anomalies 45 identified to spatial locations within the wooden member 10. The computer 34 reading the map 72 and executing commercially available optimization routines may control a computer movable saw 76 as are understood in the art to make appropriate cross cuts and rip cuts of the wooden members 10 so as to optimize the value of the wooden members 10 in the commercial market. Alternatively or in addition, the computer 34 may provide output to a commercial sorting machine to mark or direct the wooden member as to strength or grade thereby allowing more efficient use of lumbers of different strengths and in particular better use of lower grade lumbers so as to waste less wood.

It will be also understood that the detection method of the present invention may be combined with conventional visual or laser type knot and split detection equipment to augment those systems to obtain more robust detection or greater detection range.

The above description has been that of a preferred embodiment of the present invention, it will occur to those that practice the art that many modifications may be made without departing from the spirit and scope of the invention. In order to apprise the public of the various embodiments that may fall within the scope of the invention, the following claims are made.

We claim:

1. An apparatus for detecting localized anomalies in wooden members comprising:

at least one pair of opposed ultrasonic transducers positionable across an axis about wooden members to be qualified;

driving circuitry for driving a first ultrasonic transducer so as to produce an ultrasonic wave of known characteristics to produce an ultrasonic beam having a beam width in the wooden member wherein the beam width is greater than the width of the localized anomaly;

detection circuitry connected to a second ultrasonic transducer receiving the ultrasonic wave after passage through the wooden members along multiple paths within the beam width, first paths passing only through the localized anomaly and second paths not passing through the localized anomaly whereby the ultrasonic waves along the first and second paths interfere with each other to practice an interference ultrasonic wave;

an electronic computer communicating with the driving and detection circuits and executing a stored program to:
   (a) compare the interference ultrasonic wave against a standard to detect a distortion of the interference ultrasonic wave caused by an interference between portions of the ultrasonic wave passing along the first and second paths; and
   (b) provide an output indicating the presence of localized anomalies based on the comparison.

2. The apparatus of claim 1 wherein the detected distortion is selected from the group consisting of: attenuation of the total energy, change in spectral energy distribution, change in phase, time of flight, and spreading of the temporal distribution of the energy in the ultrasonic wave.

3. The apparatus of claim 2 wherein the electronic computer detects at least two distortions selected from the group consisting of: attenuation of the total energy, change in spectral energy distribution, change in phase, time of flight, and spreading of the temporal distribution of the energy in the ultrasonic wave.

4. The apparatus of claim 1 wherein the electronic computer compares the ultrasonic wave to a standard representing passage of the ultrasonic wave through wooden member of known quality.

5. The apparatus of claim 1 including means for measuring the separation of the ultrasonic transducers along the axis and wherein the electronic computer corrects the output based on the separation.

6. The apparatus of claim 1 further including means for moving the wooden members with respect to the ultrasonic transducers perpendicular to the axis in a translation direction, and wherein the output of the electronic computer is a measure of the wooden member's quality as a function of distance along the translation direction.

7. The apparatus of claim 1 further including means for moving the wooden members with respect to the ultrasonic transducers perpendicular to the axis in a translation direction, and wherein the electronic computer provides an output indicating the presence of localized anomalies also based on a change in the comparison as a function of distance along the translation direction.

8. A method of identifying localized anomalies within wooden members comprising the steps of:

(a) positioning a standard material of known characteristics between at least one pair of opposed ultrasonic tranducers;

(b) transmitting a first ultrasonic wave of known characteristics between the transducers through the standard material so as to produce a standard parameter;

(c) positioning the wooden members to be qualified between the opposed ultrasonic transducers separated along an axis;

(d) transmitting a second ultrasonic wave of known characteristics between the transducers through the wooden members to produce a beam therethrough having a beam width wherein the beam width is greater than the width of the localized anomaly;

(e) analyzing the received secodn ultrasonic wave to produce at least one measurement parameter based on distortion of the received second ultrasonic signal caused by interference between portions of the second ultrasonic wave passing through the localized anomaly and portions of the second ultrasonic wave not passing through the localized anomaly;

(f) comparing at least one measurement parameter against the standard parameter to identify the presence of a localized anomaly in the wooden member; and (g) outputting an indication of the presence of localized anomalies based on the comparison.

9. The method of claim 8 wherein the standard measurement is stored by the computer so that steps (c) through (f) may be repeated many times after once performing steps (a) and (b).

10. The method of claim 8 wherein the measurement parameter of step (e) is selected from the group consisting of: attenuation of the total energy, change in spectral energy distribution, change in phase, time of flight, and spreading of the temporal distribution of the energy in the ultrasonic wave.

11. The method of claim 8 wherein the step (e) produces two measurement parameters selected from the group consisting of: attenuation of the total energy, change in spectral energy distribution, change in phase, time of flight, and spreading of the temporal distribution of the energy in the ultrasonic wave and the comparison of step (f) compares at least two measurement parameters.

12. The method of claim 8 wherein the standard parameter measures passage of the ultrasonic wave through a clear and sound wooden member.

13. The method of claim 8 including the step of providing the output to a grading apparatus for grading the wooden member.

14. The method of claim 8 including the step of providing the output to a saw for cutting the wooden member.

* * * * *

UNITED STATES PATENT AND TRADEMARK OFFICE
CERTIFICATE OF CORRECTION

PATENT NO. : 6,029,522
DATED : 02/29/00
INVENTOR(S) : Mark E. Schafer et al.

It is certified that error appears in the above-identified patent and that said Letters Patent is hereby corrected as shown below:

Col. 7, line 45, "Er" should be $-E_r-$;

Col. 9, line 20 should continue after "y-axis" in line 19;

Col. 12, line 23, "secodn" should be –second–.

Signed and Sealed this

Eighth Day of May, 2001

Attest:

NICHOLAS P. GODICI

Attesting Officer      Acting Director of the United States Patent and Trademark Office